United States Patent [19]

Ball et al.

[11] Patent Number: 4,567,297

[45] Date of Patent: Jan. 28, 1986

[54] PREPARATION OF AQUEOUS N-METHYLOL AMIDE SOLUTIONS

[75] Inventors: Peter Ball, Emmerting; Klaus Marquardt; Manfred Selig, both of Burghausen; Günther Staudinger, Munich, all of Fed. Rep. of Germany

[73] Assignee: Wacker-Chemie GmbH, Fed. Rep. of Germany

[21] Appl. No.: 659,711

[22] Filed: Oct. 11, 1984

[30] Foreign Application Priority Data

Apr. 17, 1984 [DE] Fed. Rep. of Germany ....... 3414525

[51] Int. Cl.$^4$ ........................................... C07C 102/00
[52] U.S. Cl. .................................................. 564/208
[58] Field of Search ........................................ 564/208

[56] References Cited

U.S. PATENT DOCUMENTS

| 2,760,977 | 8/1956 | Feuer et al. | 564/208 |
| 2,864,861 | 12/1958 | Wohnsiedler et al. | 564/208 |
| 2,864,862 | 12/1958 | Sutherland et al. | 564/208 |
| 3,064,050 | 11/1962 | Saunders et al. | 564/208 |
| 3,799,910 | 3/1974 | Shingai et al. | 564/208 X |
| 3,887,618 | 6/1975 | Hein | 564/208 |
| 3,898,279 | 8/1975 | Hoke | 564/208 X |
| 4,166,828 | 9/1979 | McDonald | 564/208 X |

Primary Examiner—Paul F. Shaver
Attorney, Agent, or Firm—Charles A. Muserlian

[57] ABSTRACT

A process for the preparation of aqueous solutions of N-methylol-acrylamide and/or N-methylol-methacrylamide comprising forming a homogeneous mixture of aqueous solution of formaldehyde and aqueous solution of acrylamide and/or methacrylamide and passing the homogeneous mixture through an ion-exchange resin bed based on a styrene-divinylbenzene polymer with tertiary amino groups at an elevated temperature so that the reaction is at least 80% theoretically completed when the mixture issues from the bed, characterized in that the ion exchanger is initially in the form of its free base, the initial temperature and velocity of the homogeneous mixture being adjusted to maintain the bed temperature between 35° and 60° C. and continuing the passage of the homogeneous mixture through the exchanger bed until the bed temperature drops and/or the pH of the exiting solution is below 8.

8 Claims, No Drawings

PREPARATION OF AQUEOUS N-METHYLOL AMIDE SOLUTIONS

STATE OF THE ART

N-methylolacrylamide (NMA) and N-methylolmethacryl-amide (NMMA) are important raw materials for the production of cross-linkable polymers by radical polymerization and for textile conversion. In the following discussion, only NMA will be mentioned, but all statements made for it apply equally to NMMA. Processes for the production of NMA have long been known and all start from the reaction of acrylamide and formaldehyde. They differ in the selection of the solvent, of the formaldehyde source, and of the active base used as the catalyst. Since NMA is employed mainly in emulsion polymerization processes, aqueous NMA solutions are of special industrial importance and therefore, water is usually the preferred solvent in NMA production.

The known processes have various disadvantages. For example, when using a strong base as catalyst, a certain pH value must be adhered to very strictly. The reaction rate at 40° C. differs e.g. between pH 8.5 and pH 9.5 by a factor of 40, so that e.g. at the locus where the catalyst is added, a very rapid reaction may occur which will lead to local overheating and formation of polymeric products. This disadvantage can be avoided by using a weaker base, but then larger quantities of extraneous matter result in the product. As Japanese Patent applications No. 49-14 418 and No. 49-36 615 (Chem. Abstr., Vol. 80, 145 476 and Chem. Abstr., Vol. 81, 104 791x) show these problems can be solved by using instead of a soluble base an insoluble basic ion exchanger which is removed from the reaction mixture after the reaction.

However, these methods also still have serious disadvantages. Thus, the space-time efficiency of these methods is low, and a disproportionately large amount of the expensive ion exchanger must be used (100 ml per mole of acrylamide). Moreover, the ion exchange types named in the Japanese applications are suitable for the process only limitedly. Strongly basic ion exchangers lead to polymerization phenomena, while weakly basic products with primary and secondary amino groups react with acrylamide and lose much of their exchange capacity. Exchangers based on amineformaldehyde-phenol condensates are swelled strongly by the reaction mixture and thereby lead to severe pressure losses during passage or the reaction mixture through the exchanger bed. This, in turn, leads to increased pump costs and often to apparatus problems.

U.S. Pat. No. 3,887,618 describes an improved process for the production of NMA by reaction of a heated mixture of amide and formaldehyde solution in contact with weakly basic ion exchangers with tertiary amino groups at 40°–75° C. in which the reaction mixture must be adjusted to a pH value in the narrow range of 6.5–7.5 by addition of a substance already acting as a catalyst in itself such as triethylamine, sodium hydroxide, potassium hydroxide, etc. to avoid irreversible damage to the exchange resin. For the same purpose, only extremely short residence times of at most 5 minutes must occur because otherwise the heat of reaction can damage the exchange resin as well. It is only with these extremely short residence times that immediate overheating of the exchange layer can be prevented since cooling of the solid bed by external cooling is practically not possible. Yet in practical operation, fluctuations of the residence time are inevitable over a prolonged periods of operation but if such fluctuations or even malfunctions, e.g. due to pump failure occur, a loss of the catalyst resin and of the reaction mixture may occur, e.g. through temperature increase or through polymerization of the (meth)acrylamide; it is even inevitable in the second case. Even a planned shutdown of the plant presents great difficulties.

OBJECTS OF THE INVENTION

It was the object of the invention to find a simple economical process for the production of aqueous NMA and/or NMMA solutions which avoids the prior art disadvantages while furnishing at high space-time efficiency, a product free from impurities and polymer components, and can, if desired, even be operated continuously.

These and other objects and advantages of the invention will become obvious from the following detailed description.

THE INVENTION

The process of the invention for the preparation of aqueous solutions of N-methylol-acrylamide and/or N-methylol-methacrylamide comprising forming a homogeneous mixture of aqueous solution of formaldehyde and aqueous solution of acrylamide and/or methylacrylamide and passing the homogeneous mixture through an ion-exchange resin bed based on a styrene-divinylbenzene polymer with tertiary amino groups at an elevated temperature so that the reaction is at least 80% theoretically completed when the mixture issues from the bed, is characterized in that the ion exchanger is initially in the form of its free base, the initial temperature and velocity of homogeneous mixture being adjusted to maintain the bed temperature between 35° and 60° C. and continuing the passage of the homogeneous mixture through the exchanger bed until the bed temperature drops and/or the pH of the exiting solution is below 8.

In a preferred mode of the process, the temperature of ion exchange bed is preferably between 40° and 50° C. and is adjusted by introducing the reaction mixture into the ion exchange bed which is preferably thermally insulated from the outside at 20° to 40° C. more preferably at 20° to 35° C. and it is preferable to add the reactants in stoichiometric amounts.

In a more preferred mode of the process of the invention, the ion exchange bed is formed in a vertical column, preferably with a height to diameter ratio of 1:1 to 40:1 and the reaction mixture is passed upwardly through the bed.

The process of the invention may be carried out continuously even with commercial (meth)-acrylamide without purification with at least two vessels or columns filled with ion exchange resin connected in parallel and being separately disconnectable. In this apparatus, each bed can be disconnected as soon as its catalytic activity diminishes and can then be regenerated with an aqueous basic hydroxide solution such as alkali metal hydroxides, alkaline earth metal hydroxide and/or ammonium hydroxide while continuing the process with the other ion exchange resin bed.

It is surprising that even under the mild reaction conditions of the process of the invention equilibrium conversion can be reached, and that even at much longer residence times in the catalyst bed no changes in the catalyst or product occur, even if neutralization of the acrylamide solution is dispensed with. Moreover, even in the case of pump malfunctions, the difficulties described in the state of the art surprisingly do not occur.

The reaction mixture consists of an aqueous solution of (meth-)acrylamide and formaldehyde and the molar ratio of the two reactants is preferably 2:1 to 1:2 particularly 1:1. However, other ratios may be employed if for special reasons an excess of one component in the product is desired. When using stoichiometric quantities of formaldehyde and (meth-)acrylamide, the reaction leads to an equilibrium of NMA (NMMA), (meth-)acrylamide and formaldehyde which is approximately 83–89% of the theoretical conversion.

With the invention, commercial (meth-)acrylamide solutions can be used without further purification whose pH value is usually about 5 to 7.5 and determines the pH value of the mixture. Should the pH value be outside this normal range, adjustment into the mentioned range can, of course, be effected to prolong the life of the catalyst before the next regeneration.

The upper concentration of the reagents in water is limited by their solubility and if solid acrylamide is dissolved in 37 wt. % formalin, reactant concentration of 66 wt. % can be reached. The lower concentration is determined only by economical considerations but it is possible to react also 1 wt. % solutions. In preferred forms of realization, the reactant concentration is selected so that a 20–60 wt. % NMA solution, especially a 40–50 wt. % NMA solution, forms. If desired, there may be added to the reaction mixture a suitable polymerization inhibitor such as air, hydroquinone, monomethyl ether, benzoquinone or a similar compound well known to one skilled in the art but usually this is superfluous.

Macro-porous ion exchange products based on polystyrene cross-linked with divinyl benzene which contain free tertiary amino groups as reactive centers are used in the process and a description of such products can be found in Ullmann's Encyclopedia (Enzyklopädie der techn. Chemie), 4th edition, Verlag Chemie, Weinheim 1977, in Volume 13, page 319 Table 16 column 5. The ion exchange resins, which are usually delivered in the salt form, are transformed before the reaction, by treatment with a strong base as for example 5 wt.% sodium hydroxide solutions into their free amine form. Examples of specific macro-porous, weakly basic ion exchange resins based on styrene-divinylbenzene with tertiary amino groups are Lewatit®MP 7080 (Bayer AG, Leverkusen) and Amberlite®IRA 93 (Rohm and Haas, Philadelphia).

Because commercial acrylamide solutions often contain acid or salt containing impurities, the catalytic activity of the tertiary amino groups may diminish in time due to salt formation and this is reflected e.g. in a drop of the pH value of the draining NMA solution or in a drop in temperature of the catalyst bed. In this case, the ion exchange resin is rinsed with water and regenerated with an alkali metal hydroxide solution. To maintain continuous operation, two or more ion exchange resin columns may be arranged in parallel, of which at least one is in operation while the other or others are regenerated. As an alternative, the acryamide solution can be purified through a suitable ion exchange resin packing before the conversion which, when its catalytic capacity is exhausted, is replaced by a new one. The spent ion exchange resin packing can then be regenerated in the usual manner. The ion exchange bed(s) is/are preferably charged in column types vessels, e.g. reaction tubes.

To determine the dimensions of the reaction tubes, the pressure loss in the packing and the degree of remixing of starting components and product are used. While a long tube of small diameter results in a high pressure loss, there is danger in a short tube of large diameter that unreacted starting material will leave the column. Preferred dimensions of the exchanger bed are height-to-diameter ratios of 1:1 to 40:1, especially 10:1 to 25:1. In a preferred form of the invention already described, several exchanger tubes may be operated in parallel. The tubes may be made of any material inert to the reaction medium and examples of suitable materials are stainless steel, apparatus glass, or an inert plastic.

The tube is closed at the bottom with a sieve plate or a packing of inert fiber material and the upper tube end is secured against discharge of ion exchange material with the product stream by an analogous sieve device, preferably designed as a movable piston loaded with a light weight. By the movable arrangement of the sieve plate, swelling and contraction can be compensated for the tube is preferably mounted vertically and the flow is preferably directed upward. To avoid air bubble formation in the bed, an air bubble separator is preferably inserted before the reaction tube.

The product stream can be produced either by gravity or by pumping and it is preferred to use two pumps for (meth-)acrylamide and formalin solution and to combine the various streams in a mixing tube optionally provided with inserts. The reaction tube(s) are preferably protected against heat loss by insulation and a temperature control device may be installed on the tube section between formation of the reaction mixture and the inlet if the starting products do not have the required entrance temperature. The drain discharging the product from the reaction tube may be provided with a cooling device.

The selection of flow rate and of temperature depends on the concentration of the reaction mixture, on the activity of the ion exchange resin, on the volume of the ion exchange resin bed, and on the height-to-diameter ratio of the bed. The entrance temperature is preferably between 20° and 40° C. and the entrance temperature of the reaction mixture is selected so that the mixture heats by itself to 35° to 60° C., preferably 40° to 50° C., by the reaction enthalpy of about 16 kJ per mole of (meth-)acrylamide. This mode of operation makes temperature control of the reaction tube superfluous and avoids temperatures harmful to the exchanger.

The flow rate at a given temperature is easy to regulate by observing the percent of conversion in the end product and the conversion is preferably between 83 and 89%. Breakthrough of starting material can occur upon exhaustion of the ion exchange resin when using salt-contaminated acrylamide but can be recognized in time e.g. by the sudden drop of the pH of the outflowing solution or by the drop of the temperature of the outflowing reaction solution.

In the following examples there are described several preferred embodiments to illustrate the invention. However, it should be understood that the invention is not intended to be limited to the specific embodiments.

The butanol test is used to determine polymeric impurities wherein the polymer is mixed with four times the quantity of n-butanol and the mixture is centrifused and the height of the sediment ascertains the polymeric impurities. The "sulfite method" was used to determine the presence of free formaldehyde wherein 5 ml of a batch are pipetted into a 100 ml wide-neck Erlenmeyer flask to which 10 ml of distilled water and 5 drops of 1% by weight of thymolphthalein in methanol are added. The transition point of the indicator is then adjusted by addition of sodium hydroxide solution or hydrochloric acid solution while cooling with ice. Separately, 10 ml of a 25% by weight aqueous solution of $Na_2SO_3.7H_2O$ is adjusted to its transition point and then the two solutions are rapidly combined and titrated with 1N hydrochloric acid solution. One ml of 1N hydrochloric acid solution is equivalent to 30.03 mg of formaldehyde and rapid titration is required since slower secondary reactions also release hydroxyl ions and will cause too high values.

EXAMPLE 1

A tube 300 mm long with an inside diameter of 14.5 mm was wrapped with a 10 mm thick glass wool layer and was filled with 37 ml (22.7 g) of Amberlite ®IRA 93 in chloride form. The ion exchange resin was activated with 4% by weight sodium hydroxide solution and was washed with distilled water after which a mixture of 84.4 parts by weight of a 50% acrylamide solution, 48.5 parts by weight of a 37% formalin solution, and 9.3 parts by weight of water was pumped through the tube with an entrance temperature of 24° C. at a rate of 400 ml/h. The residence time was 7.3 min. and the conversion rate reached 87%. The product coming from the tube had a temperature of 42° to 44° C. and no polymer was detectable in the butanol test.

EXAMPLE 2

Example 1 was repeated with 9 liters of a mixture of 42.2 parts by weight of acrylamide, 48.5 parts by weight of 37% formalin, and 9.3 parts by weight of water in a continuous operation at a dosing rate of 200 ml/h with a residence time of 15 minutes. After each 900 ml of reaction solution (salt-containing acrylamide), the ion exchange resin was washed, regenerated, and washed again. The conversion was 86% and the product was free of polymer. After completion of the test which ran for 60 hours, the ion exchange resin capacity was unchanged and the resin showed no stickiness whatsoever.

EXAMPLE 3

Example 2 was repeated as a single test with 27 ml of Lewatit ®MP 7080 and a dosing rate of 250 ml/h. A conversion of 88% was reached with a residence time of 12 minutes. In the butanol test, no polymer was detectable.

EXAMPLE 4

Example 1 was repeated with 30 wt % of acrylamide solution (140 parts by weight) and variation of the entrance temperature showed that at an inlet temperature of 30° C., the results of Example 1 were obtained again.
Comparison Example A with U.S. Pat. No. 3,887,618

Example 2 was repeated, but after the 4th regeneration of the ion exchange resin the entrance temperature of the mixture was increased to 50° C. The temperature of the ion exchange resin bed immediately rose to about 70° C. and the conversion dropped to 74% and even in the following experiments with a lower entrance temperature, it reached only 78%, pointing to irreversible damage to the ion exchange resin material.
Comparison Example B Example 1 was repeated with a strongly basic ion exchange resin, namely Amberlite ®IRA 400 and after a short time, the column was clogged. It appeared that the ion exchange resin bed was completely agglutinated with polymer.
Comparison Example C Example 1 was repeated with an ion exchange resin containing also primary and secondary amino groups namely Amberlite ®IR 45 and after passage of 900 ml of reaction solution, only an average conversion of 8% was reached.
Comparison Example D Example 1 was repeated with an ion exchange resin based of amine-formaldehyde-phenol condensate namely Amberlite ®IR 4B and again, an average conversion of only 8% was obtained. During regeneration, the ion exchange resin swelled to double its volume.

Various modifications of the process of the invention may be made without departing from the spirit or scope thereof and it is to be understood that the invention is intended to be limited only as defined in the appended claims.

What we claim is:

1. A process for the preparation of aqueous solutions of N-methylol-acrylamide and/or N-methylol-methacrylamide comprising forming a homogeneous mixture of aqueous solution of formaldehyde and aqueous solution of acrylamide and/or methacrylamide and passing the homogeneous mixture through an ion-exchange resin bed based on a styrene-divinylbenzene polymer with tertiary amino groups at an elevated temperature so that the reaction is at least 80% theoretically completed when the mixture issues from the bed, characterized in that the ion exchanger is initially in the form of its free base, the initial temperature and velocity of homogeneous mixture being adjusted to maintain the bed temperature between 35° and 60° C. and continuing the passage of the homogeneous mixture through the exchanger bed until the bed temperature drops and/or the pH of the exiting solution is below 8.

2. The process of claim 1 wherein the formaldehyde and the amide reactants are used in substantially stoichiometric amounts.

3. The process of claim 1 wherein the initial temperature of the reaction mixture is 20° to 40° C.

4. The process of claim 1 wherein the ion exchange resin bed is in a vertical column with a height to diameter ratio of 1:1 to 40:1.

5. The process of claim 4 wherein the reaction mixture is introduced into the bottom of the column and passes upwardly therethrough.

6. A continuous process of claim 1 wherein there are at least two separate ion exchange resin beds separately connected in parallel to the reaction mixture whereby individual beds may be regenerated while continuing the reaction in at least one other bed.

7. The process of claim 1 wherein the methacrylamide solution is purified with an ion exchange resin bed before mixing with the formaldehyde solution.

8. The process of claim 7 wherein the reaction of formaldehyde and methacrylamide is effected continuously.

* * * * *